United States Patent
Warren et al.

(12)

(10) Patent No.: US 6,280,758 B1
(45) Date of Patent: *Aug. 28, 2001

(54) LOW-PH, ACID-CONTAINING PERSONAL CARE COMPOSITIONS WHICH EXHIBIT REDUCED STING

(75) Inventors: Raphael Warren, Cincinnati; Mannie Lee Clapp, Mason, both of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/294,574

(22) Filed: Apr. 20, 1999

Related U.S. Application Data

(63) Continuation of application No. 08/969,048, filed on Nov. 12, 1997.

(51) Int. Cl.$^7$ .......................... A01N 25/00; A61K 31/74; A61K 7/00
(52) U.S. Cl. .................. 424/404; 424/78.02; 424/78.03; 424/400; 424/401
(58) Field of Search ................................... 424/404, 400, 424/78.03, 78.02, 401

(56) References Cited

U.S. PATENT DOCUMENTS 5,989,536 * 11/1999 Deckner et al. .................. 424/78.05

* cited by examiner

*Primary Examiner*—Shelley A. Dodson
(74) *Attorney, Agent, or Firm*—Stephen T. Murphy; Tara M. Rosnell; William J. Winter

(57) ABSTRACT

The present invention relates to personal care compositions comprising from about 0.5% to about 80% of a surfactant, from about 0.1% to about 12% of a polymeric acid; and from about 3% to about 98.899% of water, wherein the composition is adjusted to a pH of from about 3.0 to about 6.0.

14 Claims, No Drawings

LOW-PH, ACID-CONTAINING PERSONAL CARE COMPOSITIONS WHICH EXHIBIT REDUCED STING

This application is a continuation of application Ser. No. 08/969,048 filed Nov. 12, 1997 now allowed.

TECHNICAL FIELD

The present invention relates to low pH, acid-containing personal care compositions which do not sting the skin upon application to the skin. Methods of minimizing or alleviating sting to the skin caused by application of acid-containing personal care compositions are also covered.

BACKGROUND OF THE INVENTION

Low pH, acid-containing personal care compositions have a variety of possible uses. Such compositions can potentially be useful for treatment of acne, treatment of dry skin, providing an essentially immediate (i.e., acute) visual improvement in skin appearance, regulating skin condition, and regulating visible and/or tactile discontinuities in skin. Perhaps most importantly, certain low pH, acid-containing compositions, especially those which also contain an antimicrobial agent, have been shown to have excellent antimicrobial efficacy.

Unfortunately, many useful acid-containing personal care compositions can cause an undesirable stinging sensation when they are applied to the skin. The problem can be especially exaggerated when the personal care composition contains high levels of acid (e.g., from about 4% to about 12% of the composition). The stinging sensation caused by these products can be a significant consumer negative; as a result of the stinging, some consumers may choose not to use a product they might otherwise have used and benefited from.

It is widely recognized that high levels of organic acids cause stinging. The patent literature has addressed the problem to a certain extent. For example, U.S. Pat. No. 4,975,217; issued Dec. 4, 1990 teaches the use of citric and lactic acid in virucidal formulas and teaches that citric acid stings less than lactic. European Patent Application 0,666,072 A2, published on Aug. 7, 1995 teaches that rosmarrinic acid can be employed in acid-containing compositions to reduce sting.

It has now been found, however, that sting is vastly reduced and, in some cases, completely eliminated when certain polymeric acids are employed in place of other organic acids in low pH, acid-containing personal care compositions. WO 95/32705, published Dec. 7, 1995, teaches generally the use of these polymeric acids, as well as other organic acids, in low pH, acid-containing personal care compositions. However, low pH, acid-containing personal care compositions which contain polymeric acids are not specifically taught and polymeric acids are not taught as reducing sting.

It is an object of the present invention, therefore, to provide low pH, acid-containing personal care compositions which cause significantly less stinging when they are applied to the skin compared to other low pH, acid-containing personal care composition taught in the prior art.

SUMMARY OF THE INVENTION

The present invention relates to personal care compositions comprising from about 0.05% to about 80% of a surfactant; from about 0.1% to about 12% of a polymeric acid; and from about 3% to about 98.899% of water; wherein the composition is adjusted to a pH of from about 3.0 to about 6.0. The present invention also relates to a method for minimizing or alleviating sting to the skin caused by acid-containing personal care compositions, which method comprises applying the low pH acid-containing personal care composition of the present invention to the skin.

DETAILED DESCRIPTION OF THE INVENTION

The present invention relates to personal care compositions comprising from about 0.05% to about 80% of a surfactant; from about 0.1% to about 12% of a polymeric acid; and from about 3% to about 98.899% of water; wherein the composition is adjusted to a pH of from about 3.0 to about 6.0. The present invention also relates to methods for minimizing or alleviating sting, burn or itching to the skin caused by acid-containing personal care compositions, which method comprises applying the low pH acid-containing personal care composition of the present invention to the skin.

The low pH, acid-containing personal care compositions of the present invention cause minimal or no stinging when applied to the skin. As used herein, "personal care compositions" refers to rinse-off personal cleansing compositions, wipes compositions, and topical, leave-on personal care compositions. The term "rinse-off" is used herein to mean that the composition is used in a context whereby the composition is ultimately rinsed or washed from the treated surface (e.g., skin or hair) either after or during the application of the product. Rinse-off personal cleansing compositions include, for example, liquid handsoaps, liquid shower gels, bar soaps, and shampoos. As used herein, "leave-on" personal care compositions are compositions (e.g., lotions, creams and gels) which are applied to skin, directly or indirectly, and not rinsed away. As used herein, "wipes compositions" refer to products in which a sheet of porous or absorbent material has been impregnated with a cleansing composition. Typically, wipes compositions are rubbed over a surface (e.g., skin) to clean the surface. Alternately, the wipe composition can be in the form of a feminine pad and the personal care composition can be applied to the pad to provide antimicrobial or deodorancy benefits.

In one embodiment of the wipes compositions of the present invention, the porous or absorbent material can comprise woven or nonwoven fabrics derived from "oriented" or carded fibrous webs composed of textile-length fibers, the major proportion of which are oriented predominantly in one direction are suitable for use herein. These fabrics can be in the form of, for example, wipes or towelettes, including baby wipes, feminine wipes and the like.

The nonwoven cloth substrates are generally adhesively bonded fibers or filamentous products having a web or carded fiber structure (when the fiber strength is suitable to allow carding) or comprising fibrous mats in which the fibers or filaments are distributed haphazardly or in random array (i.e., an array of fibers in a carded web where partial orientation of the fibers is frequently present, as well as a completely haphazard distributional orientation), or substantially aligned. The fibers or filaments can be natural (e.g., wool, silk, jute, hemp, cotton, linen, sisal, or ramie) or synthetic (e.g., rayon, cellulose ester, polyvinyl derivatives, polyolethins, polyamides, or polyesters) as have been described hereinabove. These nonwoven materials are generally described in Riedel "Nonwoven Bonding Methods and Materials", *Nonwoven World*, (1987).

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

I. INGREDIENTS

The low-pH, acid-containing personal care compositions of the present invention comprise a surfactant, a polymeric acid and water. The personal care compositions of the present invention cause significantly less stinging when applied to the skin than other low-pH, acid-containing compositions. Each of the ingredients comprising the low-sting personal care compositions of the present invention are described in detail as follows:

A. POLYMERIC ACID

The personal care compositions of the present invention comprise from about 0.1% to about 12%, preferably from about 1% to about 12%, more preferably from about 2.5% to about 12%, and most preferably from about 4% to about 12%, based on the weight of the personal care composition, of a polymeric acid. As used herein, the term "polymeric acid" refers to an acid with repeating units of carboxylic acid groups joined together into one chain. Suitable polymeric acids can include homopolymers, copolymers and terpolymers, but must include at least 30 mole % carboxylic acid groups. Specific examples of suitable polymeric acids useful herein include straight poly(acrylic) acid and its copolymers, both ionic and nonionic, (e.g., maleic-acrylic, sulfonic-acrylic, and styrene-acrylic copolymers), cross-linked poly(acrylic) acids having a molecular weight of less than 250,000, preferably less than about 100,000, poly (α-hydroxy) acids, poly (methacrylic) acid, and naturally occurring polymeric acids such as carageenic acid, carboxy methyl cellulose, and alginic acid. Straight-chain poly (acrylic) acids are especially preferred for use herein.

pH

The pH of the personal care compositions herein typically ranges from about 3.0 to about 6.0, preferably from about 3.0 to about 5.0 and more preferably from about 3.5 to about 4.5. The compositions are preferably buffered to achieve these pH levels.

B. THE SURFACTANT

The personal care compositions of the present invention comprise from about 0.05 to about 80% of a surfactant. Liquid, rinse-off compositions of the present invention typically comprise from about 1% to about 80%, preferably from about 3% to about 50%, and more preferably from about 5% to about 25%, based on the weight of the personal care composition, of a surfactant. Solid bar embodiments of the present invention preferably comprise from about 10% to about 70%, and more preferably from about 20% to about 60% of a surfactant. Leave-on compositions typically comprise from about 0.05% to about 10%, preferably from about 0.1% to about 2%, more preferably from about 0.2% to about 1% by weight of the composition of a surfactant.

The surfactant employed in the compositions herein can be selected from the group consisting of anionic surfactants, nonionic surfactants, cationic surfactants, amphoteric surfactants and mixtures thereof.

In a preferred embodiment of the present invention, at least one lathering, anionic surfactant is employed. Nonlimiting examples of anionic lathering surfactants useful in the compositions of the present invention are disclosed in McCutcheon's, *Detergents and Emulsifiers*, North American edition (1990), published by The Manufacturing Confectioner Publishing Co.; McCutcheon's, *Functional Materials*, North American Edition (1992); and U.S. Pat. No. 3,929,678, to Laughlin et al., issued Dec. 30, 1975, all of which are incorporated by reference.

A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and mixtures thereof. Mixtures of anionic surfactants can be used effectively in the present invention.

C. WATER

The personal care compositions of the present invention comprise from about 35% to about 98.899% water. Liquid, rinse-off compositions preferably from about 45% to about 98%, more preferably from about 55% to about 97.5%, and most preferably from about 65% to about 95.99% water. Solid bar embodiments of the present invention preferably comprise from about 2% to about 25%, more preferably from about 3% to about 20% and most preferably from about 5% to about 15% water. Leave-on compositions preferably comprise from about 5% to about 97.5%, more preferably from about 38% to about 95% water.

D. PREFERRED OPTIONAL INGREDIENTS

1. Antimicrobial Active

The personal care compositions of the present invention preferably comprise an antimicrobial active. Typically, these compositions comprise from about 0.001% to about 5%, preferably from about 0.01% to about 2%, more preferably from about 0.05% to about 1.5% and more preferably from about 0.1% to about 1.0%, by weight of the composition, of an antimicrobial active. The exact amount of antibacterial active to be used in the compositions will depend on the particular active utilized since actives vary in potency.

Given below are examples of antimicrobial agents which are useful in the present invention.

Pyrithiones, especially the zinc complex (ZPT)
Octopirox®
Dimethyldimethylol Hydantoin (Glydant®)
Methylchloroisothiazolinone/methylisothiazolinone (Kathon CG®)
Sodium Sulfite
Sodium Bisulfite
Imidazolidinyl Urea (Germall 115®)
Diazolidinyl Urea (Germall II®)
Benzyl Alcohol
2-Bromo-2-nitropropane-1,3-diol (Bronopol®)
Formalin (formaldehyde)
Iodopropenyl Butylcarbamate (Polyphase P100®)
Chloroacetamide
Methanamine
Methyldibromonitrile Glutaronitrile (1,2-Dibromo-2,4-dicyanobutane or Tektamer®)
Glutaraldehyde
5-bromo-5-nitro-1,3-dioxane (Bronidox®)
Phenethyl Alcohol
o-Phenylphenol/sodium o-phenylphenol
Sodium Hydroxymethylglycinate (Suttocide A®)
Polymethoxy Bicyclic Oxazolidine (Nuosept C®)
Dimethoxane
Thimersal Dichlorobenzyl Alcohol
Captan
Chlorphenenesin
Dichlorophene
Chlorbutanol
Glyceryl Laurate
Halogenated Diphenyl Ethers
    2,4,4'-trichloro-2'-hydroxy-diphenyl ether (Triclosan® or TCS)
    2,2'-dihydroxy-5,5'-dibromo-diphenyl ether
Phenolic Compounds
    Phenol
    2-Methyl Phenol
    3-Methyl Phenol
    4-Methyl Phenol
    4-Ethyl Phenol
    2,4-Dimethyl Phenol
    2,5-Dimethyl Phenol
    3,4-Dimethyl Phenol
    2,6-Dimethyl Phenol
    4-n-Propyl Phenol
    4-n-Butyl Phenol
    4-n-Amyl Phenol
    4-tert-Amyl Phenol
    4-n-Hexyl Phenol
    4-n-Heptyl Phenol
Mono- and Poly-Alkyl and Aromatic Halophenols
    p-Chlorophenol
    Methyl p-Chlorophenol
    Ethyl p-Chlorophenol
    n-Propyl p-Chlorophenol
    n-Butyl p-Chlorophenol
    n-Amyl p-Chlorophenol
    sec-Amyl p-Chlorophenol
    n-Hexyl p-Chlorophenol
    Cyclohexyl p-Chlorophenol
    n-Heptyl p-Chlorophenol
    n-Octyl p-Chlorophenol
    o-Chlorophenol
    Methyl o-Chlorophenol
    Ethyl o-Chlorophenol
    n-Propyl o-Chlorophenol
    n-Butyl o-Chlorophenol
    n-Amyl o-Chlorophenol
    tert-Amyl o-Chlorophenol
    n-Hexyl o-Chlorophenol
    n-Heptyl o-Chlorophenol
    o-Benzyl p-Chlorophenol
    o-Benxyl-m-methyl p-Chlorophenol
    o-Benzyl-m, m-dimethyl p-Chlorophenol
    o-Phenylethyl p-Chlorophenol
    o-Phenylethyl-m-methyl p-Chlorophenol
    3-Methyl p-Chlorophenol
    3,5-Dimethyl p-Chlorophenol
    6-Ethyl-3-methyl p-Chlorophenol
    6-n-Propyl-3-methyl p-Chlorophenol
    6-iso-Propyl-3-methyl p-Chlorophenol
    2-Ethyl-3,5-dimethyl p-Chlorophenol
    6-sec-Butyl-3-methyl p-Chlorophenol
    2-iso-Propyl-3,5-dimethyl p-Chlorophenol
    6-Diethylmethyl-3-methyl p-Chlorophenol
    6-iso-Propyl-2-ethyl-3-methyl p-Chlorophenol
    2-sec-Amyl-3,5-dimethyl p-Chlorophenol
    2-Diethylmethyl-3,5-dimethyl p-Chlorophenol
    6-sec-Octyl-3-methyl p-Chlorophenol
    p-Chloro-m-cresol
    p-Bromophenol
    Methyl p-Bromophenol
    Ethyl p-Bromophenol
    n-Propyl p-Bromophenol
    n-Butyl p-Bromophenol
    n-Amyl p-Bromophenol
    sec-Amyl p-Bromophenol
    n-Hexyl p-Bromophenol
    Cyclohexyl p-Bromophenol
    o-Bromophenol
    tert-Amyl o-Bromophenol
    n-Hexyl o-Bromophenol
    n-Propyl-m,m-Dimethyl o-Bromophenol
    2-Phenyl Phenol
    4-Chloro-2-methyl phenol
    4-Chloro-3-methyl phenol
    4-Chloro-3,5-dimethyl phenol
    2,4-Dichloro-3,5-dimethylphenol
    3,4,5,6-Terabromo-2-methylphenol
    5-Methyl-2-pentylphenol
    4-Isopropyl-3-methylphenol
    Para-chloro-meta-xylenol (PCMX)
    Chlorothymol
    Phenoxyethanol
    Phenoxyisopropanol
    5-Chloro-2-hydroxydiphenylmethane
Resorcinol and its Derivatives
    Resorcinol
    Methyl Resorcinol
    Ethyl Resorcinol
    n-Propyl Resorcinol
    n-Butyl Resorcinol
    n-Amyl Resorcinol
    n-Hexyl Resorcinol
    n-Heptyl Resorcinol
    n-Octyl Resorcinol
    n-Nonyl Resorcinol
    Phenyl Resorcinol
    Benzyl Resorcinol
    Phenylethyl Resorcinol
    Phenylpropyl Resorcinol
    p-Chlorobenzyl Resorcinol
    5-Chloro 2,4-Dihydroxydiphenyl Methane
    4'-Chloro 2,4-Dihydroxydiphenyl Methane
    5Bromo 2,4-Dihydroxydiphenyl Methane
    4'-Bromo 2,4-Dihydroxydiphenyl Methane
Bisphenolic Compounds
    2,2'-Methylene bis (4-chlorophenol)
    2,2'-Methylene bis (3,4,6-trichlorophenol)

2,2'-Methylene bis (4-chloro-6-bromophenol)
bis (2-hydroxy-3,5-dichlorophenyl) sulphide
bis (2-hydroxy-5-chlorobenzyl)sulphide
Benzoic Esters (Parabens)
   Methylparaben
   Propylparaben
   Butylparaben
   Ethylparaben
   Isopropylparaben
   Isobutylparaben
   Benzylparaben
   Sodium Methylparaben
   Sodium Propylparaben
Halogenated Carbanilides
   3,4,4'-Trichlorocarbanilides (Triclocarban® or TCC)
   3-Trifluoromethyl-4,4'-dichlorocarbanilide
   3,3',4-Trichlorocarbanilide Another class of antibacterial agents, which are useful in the present invention, are the so-called "natural" antibacterial actives, referred to as natural essential oils. These actives derive their names from their natural occurrence in plants. Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea origanum, *Hydastis carradensis, Berberidaceae daceae,* Ratanhiae and *Curcuma longa.* Also included in this class of natural essential oils are the key chemical components of the plant oils which have been found to provide the antimicrobial benefit. These chemicals include, but are not limited to anethol, catechole, camphene, thymol, eugenol, eucalyptol, ferulic acid, farnesol, hinokitiol, tropolone, limonene, menthol, methyl salicylate, carvacol, terpineol, verbenone, berberine, ratanhiae extract, caryophellene oxide, citronellic acid, curcumin, nerolidol and geraniol.

Additional active agents are antibacterial metal salts. This class generally includes salts of metals in groups 3b–7b, 8 and 3a–5a. Specifically are the salts of aluminum, zirconium, zinc, silver, gold copper, lanthanum, tin, mercury, bismuth, selenium, strontium, scandium, yttrium, cerium, praseodymiun, neodymium, promethum, samarium, europium, gadolinium, terbium, dysprosium, holmium, erbium, thulium, ytterbium, lutetium and mixtures thereof.

Preferred antimicrobial agents for use herein are the broad spectrum actives selected from the group consisting of Triclosan®, Triclocarban®, Octopirox®, PCMX, ZPT, natural essential oils and their key ingredients, and mixtures thereof. The most preferred antimicrobial active for use in the present invention is Triclosan®.

2. Lipophilic Skin Moisturizing Agent

Lipophilic skin moisturizing agents are preferably included in the compositions herein in an amount ranging from about 0.1% to about 30%, preferably from about 1% to about 30% more preferably from about 3% to about 25%, most preferably from about 5% to about 25% of the composition.

Two types of rheological parameters are used to define the lipophilic skin moisturizing agent used herein. The viscosity of the lipophilic skin moisturizing agent is represented by consistency (k) and shear index (n). The lipophilic skin moisturizing agents for use herein typically have a consistency (k) ranging from about 5 to about 5,000 poise, preferably from about 10 to about 3,000 poise, more preferably from about 50 to about 2,000 poise, as measured by the Consistency (k) Method hereinafter set forth in the Analytical Methods section. Suitable lipophilic skin moisturizing agents for use herein further have a shear index (n) ranging from about 0.01 to about 0.9, preferably from about 0.1 to about 0.5, more preferably from about 0.2 to about 0.5, as measured by the Shear Index Method hereinafter set forth in the Analytical methods section.

While not being bound by any theory, it is believed that lipophilic skin moisturizing agents having rheology properties other than those defined herein are either too easily emulsified and hence will not deposit, or are too "stiff" to adhere or deposit on to skin and provide a moisturization benefit. In addition, the rheological properties of the lipophilic skin moisturizing agent are also important to user perception. Some lipophilic skin moisturizing agents, on deposition to the skin, are considered too sticky and are not preferred by the user.

In some cases, the lipophilic skin moisturizing agent can also desirably be defined in terms of its solubility parameter, as defined by *Vaughan in Cosmetics and Toiletries*, Vol. 103, p. 47–69, October 1988. A lipophilic skin moisturizing agent having a Vaughan solubility Parameter (VSP) from 5 to 10, preferably from 5.5 to 9 is suitable for use in the liquid personal cleansing compositions herein.

A wide variety of lipid type materials and mixtures of materials are suitable for use as the carrier in the antimicrobial personal cleansing compositions of the present invention. Preferably, the lipophilic skin conditioning agent is selected from the group consisting of hydrocarbon oils and waxes, silicones, fatty acid derivatives, cholesterol, cholesterol derivatives, di- and tri-glycerides, vegetable oils, vegetable oil derivatives, liquid nondigestible oils such as those described in U.S. Pat. No. 3,600,186 to Mattson; Issued Aug. 17, 1971 and U.S. Pat. Nos. 4,005,195 and 4,005,196 to Jandacek et al; both issued Jan. 25, 1977, all of which are herein incorporated by reference, or blends of liquid digestible or nondigestible oils with solid polyol polyesters such as those described in U.S. Pat. No. 4,797, 300 to Jandacek; issued Jan. 10, 1989; U.S. Pat. Nos. 5,306,514, 5,306,516 and 5,306,515 to Letton; all issued Apr. 26, 1994, all of which are herein incorporated by reference, and acetoglyceride esters, alkyl esters, alkenyl esters, lanolin and its derivatives, milk tri-glycerides, wax esters, beeswax derivatives, sterols, phospholipids and mixtures thereof. Fatty acids, fatty acid soaps and water soluble polyols are specifically excluded from our definition of a lipophilic skin moisturizing agent.

Hydrocarbon oils and waxes: Some examples are petrolatum, mineral oil microcrystalline waxes, polyalkenes (e.g. hydrogenated and nonhydrogenated polybutene and polydecene), paraffins, cerasin, ozokerite, polyethylene and perhydrosqualene. Blends of petrolatum and hydrogenated and nonhydrogenated high molecular weight polybutenes wherein the ratio of petrolatum to polybutene ranges from about 90:10 to about 40:60 are also suitable for use as the lipid skin moisturizing agent in the compositions herein.

Silicone Oils: Some examples are dimethicone copolyol, dimethylpolysiloxane, diethylpolysiloxane, high molecular weight dimethicone, mixed C1–C30 alkyl polysiloxane, phenyl dimethicone, dimethiconol, and mixtures thereof. More preferred are non-volatile silicones selected from dimethicone, dimethiconol, mixed C1–C30 alkyl polysiloxane, and mixtures thereof. Nonlimiting examples of silicones useful herein are described in U.S. Pat. No. 5,011,681, to Ciotti et al., issued Apr. 30, 1991, which is incorporated by reference.

Di and tri-glycerides: Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Acetoglyceride esters are used and an example is acetylated monoglycerides.

Lanolin and its derivatives are preferred and some examples are lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate.

It is most preferred when at least 75% of the lipophilic skin conditioning agent is comprised of lipids selected from the group consisting: petrolatum, blends of petrolatum and high molecular weight polybutene, mineral oil, liquid non-digestible oils (e.g. liquid cottonseed sucrose octaesters) or blends of liquid digestible or nondigestible oils with solid polyol polyesters (e.g. sucrose octaesters prepared from C22 fatty acids) wherein the ratio of liquid digestible or nondigestible oil to solid polyol polyester ranges from about 96:4 to about 80:20, hydrogenated or nonhydrogenated polybutene, microcrystalline wax, polyalkene, paraffin, cerasin, ozokerite, polyethylene, perhydrosqualene; dimethicones, alkyl siloxane, polymethylsiloxane, methylphenylpolysiloxane and mixtures thereof. When as blend of petrolatum and other lipids is used, the ratio of petrolatum to the other selected lipids (hydrogenated or unhydrogenated polybutene or polydecene or mineral oil) is preferably from about 10:1 to about 1:2, more preferably from about 5:1 to about 1:1.

3. Stabilizers

When a lipophilic skin moisturizing agent is employed in the compositions herein, a stabilizer is also included at a level ranging from about 0.1% to about 10%, preferably from about 0.1% to about 8%, more preferably from about 0.1% to about 5% by weight of the composition.

The stabilizer is used to form a crystalline stabilizing network in the composition that prevents the lipophilic skin moisturizer agent droplets from coalescing and phase splitting in the product. The network exhibits time dependent recovery of viscosity after shearing (e.g., thixotropy).

The stabilizer used herein are not surfactants. The stabilizers provide improved shelf and stress stability, but allow the to separate upon lathering, and thereby provide for increased deposition of the lipophilic skin moisturizing agent onto the skin. This is particularly true when the cleansing emulsions of the present invention are used in conjunction with a polymeric diamond meshed sponge implement such as that described in Campagnoli; U.S. Pat. No. 5,144,744; Issued Sep. 8, 1992, herein incorporated by reference.

In one embodiment of the present invention, the stabilizer employed in the compositions herein comprises a crystalline, hydroxyl-containing stabilizer. This stabilizer can be a hydroxyl-containing fatty acid, fatty ester or fatty soap water-insoluble wax-like substance or the like.

The crystalline, hydroxy-containing stabilizer is selected from the group consisting of:

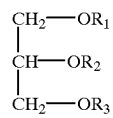
(i)

wherein

$R_2$ is $R_1$ or H
$R_3$ is $R_1$ or H
$R_4$ is $C_{0-20}$ Alkyl
$R_5$ is $C_{0-20}$ Alkyl,
$R_6$ is $C_{0-20}$ Alkyl
$R_4+R_5+R_6=C_{10-22}$
and wherein $1 \leq x+y \leq 4$;

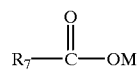
(ii)

wherein
$R_7$ is $-R_4(CHOH)_xR_5(CHOH)_yR_6$
M is $Na^+$, $K^+$ or $Mg^{++}$, or H; and
iii) mixtures thereof;

Some preferred hydroxyl-containing stabilizers include 12-hydroxystearic acid, 9,10-dihydroxystearic acid, tri-9, 10-dihydroxystearin and tri-12-hydroxystearin (hydrogenated castor oil is mostly tri-12-hydroxystearin). Tri-12-hydroxystearin is most preferred for use in the emulsion compositions herein.

When these crystalline, hydroxyl-containing stabilizers are utilized in the compositions herein, they are typically present at from about 0.1% to 10%, preferably from 0.1% to 8%, more preferably from 0.1% to about 5% of the composition. The stabilizer is insoluble in water under ambient to near ambient conditions.

Alternatively, the stabilizer employed in the compositions herein can comprise a polymeric thickener. When polymeric thickeners as the stabilizer in the compositions herein, they are typically included in an amount ranging from about 0.01% to about 5%, preferably from about 0.3% to about 3%, by weight of the composition. The polymeric thickener is preferably an anionic, nonionic, cationic or hydrophobically modifier polymer selected from the group consisting of cationic polysaccharides of the cationic guar gum class with molecular weights of 1,000 to 3,000,000, anionic, cationic, and nonionic homopolymers derived from acrylic and/or methacrylic acid, anionic, cationic, and nonionic cellulose resins, cationic copolymers of dimethyldialkylammonium chloride, and acrylic acid, cationic homopolymers of dimethylalkylammonium chloride, cationic polyalklene, and ethoxypolyalkylene imines, polyethylene glycol of molecular weight from 100,000 to 4,000,000, and mixtures thereof. Preferably, the polymer is selected from the group consisting of sodium polyacrylate, hydroxy ethyl cellulose, cetyl hydroxy ethyl cellulose, and polyquaternium 10.

Alternatively, the stabilizer employed in the compositions herein can comprise C10–C22 ethylene glycol fatty acid esters. C10–C22 ethylene glycol fatty acid esters can also desirably by employed in combination with the polymeric thickeners hereinbefore described. The ester is preferably a diester, more preferably a C14–C18 diester, most preferably ethylene glycol distearate. When C10–C22 ethylene glycol fatty acid esters are utilized as the stabilizer in the personal cleansing compositions herein, they are typically present at from about 3% to about 10%, preferably from about 5% to about 8%, more preferably from about 6% to about 8% of the personal cleansing compositions.

Another class of stabilizer which can be employed in the compositions of the present invention comprises dispersed amorphous silica selected from the group consisting of fumed silica and precipitated silica and mixtures thereof. As used herein the term "dispersed amorphous silica" refers to small, finely divided non-crystalline silica having a mean agglomerate particle size of less than about 100 microns.

Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates. precipitated silicas and silica gels are generally made in aqueous solution. See, Cabot Technical Data Pamphlet TD-100 entitled "CAB-O-SIL® Untreated Fumed Silica Properties and Functions", Oct. 1993, and Cabot Technical Dat Pamphlet TD-104 entitled "CAB-O-SIL® Fumed Silica in Cosmetic and Personal Care Products", March 1992, both of which are herein incorporated by reference.

The fumed silica preferably has a mean agglomerate particle size ranging from about 0.1 microns to about 100 microns, preferably from about 1 micron to about 50 microns, and more preferably from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and most preferably from about 0.2 microns to about 0.3 microns. The silica preferably has a surface area greater than 50 sq. m/gram, more preferably greater than about 130 sq. m/gram, most preferably greater than about 180 sq. m/gram.

When amorphous silicas are used as the stabilizer herein, they are typically included in the compositions at levels ranging from about 0.1% to about 10%, preferably from about 0.25% to about 8%, more preferably from about 0.5% to about 5%.

A fourth class of stabilizer which can be employed in the compositions of the present invention comprises dispersed smectite clay selected from the group consisting of bentonite and hectorite and mixtures thereof. Bentonite is a colloidal aluminum clay sulfate. See Merck Index, Eleventh Edition, 1989, entry 1062, p. 164, which is incorporated by reference. Hectorite is a clay containing sodium, magnesium, lithium, silicon, oxygen, hydrogen and flourine. See Merck Index, eleventh Edition, 1989, entry 4538, p. 729, which is herein incorporated by reference.

When smectite clay is employed as the stabilizer in the compositions of the present invention, it is typically included in amounts ranging from about 0.1% to about 10%, preferably from about 0.25% to about 8%, more preferably from about 0.5% to about 5%.

Other known stabilizer, such as fatty acids and fatty alcohols, can also be employed in the compositions herein. Palmitic acid and lauric acid are especially preferred for use herein.

4. Mildness Enhancers

Mildness enhancer can desirably be added to the personal care compositions of the present invention. Mildness enhancers include cationic and nonionic polymers, co-surfactants, moisturizers and mixtures thereof. Polymers useful herein include polyethylene glycols, polypropylene glycols, hydrolyzed silk proteins, hydrolyzed milk proteins, hydrolyzed keratin proteins, guar hydroxypropyltrimonium chloride, polyquats, silicone polymers and mixtures thereof. When used, the mildness enhancing polymers comprise from about 0.1% to about 1%, preferably from about 0.2% to about 1.0%, and more preferably from about 0.2% to about 0.6%, by weight of the composition. Co-surfactants useful herein include nonionic surfactants such as the Genapol® 24 series of ethoxylated alcohols, POE(20) sorbitan monooleate (Tween® 80), polyethylene glycol cocoate and Pluronic® propylene oxide/ethylene oxide block polymers, and amphoteric surfactants such as alkyl betaines, alkyl sultaines, alkyl amphoacetates, alkyl amphodiacetates, alkyl amphopropionates, and alkyl amphodipropionates. When used, the mildness enhancing cosurfactants comprise from about 20% to about 70%, preferably from about 20% to about 50%, by weight of the surfactant, of the composition.

E. OTHER OPTIONAL INGREDIENTS

The compositions of the present invention can comprise a wide range of optional ingredients. The *CTFA International Cosmetic Ingredient Dictionary,*Sixth Edition, 1995, which is incorporated by incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives, colorants, cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention Ingredients are identified by chemical or CTFA name.

Liquid Handsoap

| Component | 1 | 2 | 3 | 4 | 5 |
|---|---|---|---|---|---|
| Ammonium Lauryl Sulfate | 0.00 | 2.60 | 0.00 | 3.1 | 3.0 |
| Sodium Lauryl Sulfate | 3.50 | 0.00 | 3.50 | 0.00 | 0.00 |
| Ammonium Laureth-3 Sulfate | 0.00 | 7.90 | 0.00 | 6.6 | 6.0 |
| Sodium Laureth-3 Sulfate | 7.00 | 0.00 | 7.00 | 0.00 | 0.00 |
| Sodium Myristyl Sulfate | 0.00 | 0.00 | 0.00 | 0.00 | 0.00 |
| Cocamidopropyl Betaine | 0.00 | 0.00 | 0.00 | 0.00 | 0.00 |
| Sodium Lauroamphoacetate | 0.00 | 0.00 | 5.25 | 5.00 | 5.0 |
| poly(acrylic) acid/polyacrylate* | 8.00 | 6.00 | 8.00 | 8.00 | 8.00 |
| Petrolatum | 0.00 | 0.00 | 0.00 | 12.0 | 12.0 |
| Tri-hydroxysearin | 0.00 | 0.00 | 0.00 | 0.25 | 0.25 |
| Lauric Acid | 0.00 | 0.00 | 0.00 | 1.5 | 1.5 |
| Polyquaternium 10 | 0.40 | 0.40 | 0.40 | 0.10 | 0.10 |
| Para-chloro-meta-xylenol | 1.50 | 0.00 | 0.00 | 0.00 | 0.00 |
| Triclosan ® | 0.00 | 0.50 | 0.00 | 0.00 | 0.50 |
| Perfume | 1.0 | 1.0 | 1.0 | 0.4 | 0.0 |
| Miscellaneous | 0.00 | 0.00 | 0.00 | 0.00 | 1.33 |
| Water | Q.S. | Q.S. | Q.S. | Q.S. | Q.S. |
| pH | 4.0 | 3.7 | 4.0 | 4.0 | 4.0 |

*Polyacrylate is K-7058 sold by B. F. Goodrich

Procedure for Making Liquid Handsoap Examples

1) Examples 1–3

Add all but 5 weight percent water to mix tank. Add surfactants to mix tank. Heat materials to 155° F.±10° F. and mix until dissolved. Cool to less than 100° F., add acid and antibacterial active and perfumes. Mix until materials are dissolved. Adjust pH to target with required buffer (NaOH or sodium salt of acid). Add remaining water to complete product.

2) Examples 4 and 5

Add all ingredients except petrolatum, active and perfume together and heat to the point necessary to melt the stabilizer (approximately 190° F. for trihydroxystearin). Cool to below 115° F. and add active, petrolatum and perfume. Adjust final pH using NaOH or buffer salt. Add remaining water to complete product.

Shower Gel

| Component | 1 | 2 | 3 |
|---|---|---|---|
| Sodium or Ammonium Lauryl Sulfate | 6.30 | 3.50 | 3.15 |
| Sodium or Ammonium Laureth-3 Sulfate | 4.20 | 7.00 | 9.45 |
| Sodium or Ammonium Lauroamphoacetate | 0.00 | 5.25 | 5.40 |
| Cocoamide MEA | 2.80 | 2.80 | 0.00 |
| Cocamidopropyl Betaine | 0.00 | 0.00 | 0.00 |
| Poly(acrylic) acid/polyacrylate* | 6.50 | 8.00 | 6.50 |
| Triclocarban ® | 0.00 | 0.00 | 0.00 |
| Triclosan ® | 1.00 | 0.00 | 0.00 |
| Soybean Oil | 0.00 | 8.00 | 0.00 |
| Petrolatum | 0.00 | 0.00 | 16.50 |
| Tri-hydroxystearin | 0.00 | 0.00 | 1.00 |
| Lauric Acid | 0.00 | 0.00 | 1.00 |
| Palmitic Acid | 2.20 | 0.00 | 0.00 |
| Polyquaternium 10 | 0.30 | 0.30 | 0.30 |
| Miscellaneous | 8.28 | 1.75 | 1.61 |
| Water | Q.S. | Q.S. | Q.S. |
| pH | 4.0 | 3.7 | 4.0 |

*poly(acrylic) acid/polyacrylate is K7058 sold by B. F. Goodrich

Procedure for Making Shower Gels

1) Examples 1 and 2

Add moisturizing oils and co-surfactants together and heat ingredients to 130–140° F. until dissolved (step can be skipped for products not containing oils). In another container add primary surfactants, acid buffer salt, preservatives, viscosity builder (salt), and polymer. Heat to 130–140° F. until dissolved. Combine two mixtures (or use single mixture if no oils are present) when both are 130–140° F., then begin cooling. When mixture is below 115° F., add, antibacterial active and perfume. Adjust final pH using NaOH or remaining buffer salt. Add remaining water to complete product.

2) Example 3

Add all ingredients except petrolatum, antimicrobial active and perfume together and heat to the point necessary to melt the stabilizer (approximately 190° F. for trihydroxystearin). Cool to below 115° F. and add active, petrolatum and perfume. Adjust final pH using NaOH or buffer salt. Add remaining water to complete product.

| Component | Ex. 1 |
|---|---|
| Mineral oil | 1.00% |
| Propylene glycol | 1.00% |
| Ammnonium Lauryl Sulfate | 0.60% |
| poly(acrylic) acid/sodium polyacrylate* | 2.5% |
| Steareth 20 | 0.08% |
| Steareth 2 | 0.07% |
| Oleth 20 | 0.08% |
| Oleth 2 | 0.07% |
| Miscellaneous | 0.36% |
| Water | q.s. |
| pH | 3.8 |

*Acumer 1020 sold by Rohm & Haas

Procedure for Making Antimicrobial Cleansing Composition Example

Premix mineral oil, propylene glycol, steareth 2 and 20, oleth 2 and 20, and 50%, by weight of the oil, glycol, steareth and oleth materials, water to a premix vessel. Heat to 165° F.±10° F. Add additional 50%, by weight of the oil, glycol, steareth and oleth materials, of water to the premix tank.

Add all but 5 weight percent of remaining water to second mix tank. If required, add premix to the mix tank. Add surfactants to mix tank. Heat materials to 155° F.±10° F. and mix until dissolved. Cool to less than 100° F., add acid and perfumes. Mix until materials are dissolved. Adjust pH to target with required buffer (NaOH or buffer salt). Add remaining water to complete product.

Procedure for Making Antimicrobial Wipe Examples

The preceding Composition is impregnated onto absorbent sheets as follows:

The Composition is impregnated onto a wet and air laid woven absorbent sheet comprised of 85% cellulose and 15% polyester at 260% by weight of the absorbent sheet by pouring the composition onto the sheet via a cup.

The Composition is impregnated onto a wet and air laid woven absorbent sheet comprised of 100% cellulose at 260% by weight of the sheet by pouring the composition onto the sheet via a cup.

The Composition is impregnated onto separate wet and air laid nonwoven absorbent sheets comprised of 50% cellulose and 50% polyester at 260% by weight of the sheet by pouring the composition onto the sheets via a cup.

What is claimed is:

1. A wipe composition comprising a porous or absorbent sheet impregnated with a personal care composition, wherein the personal care composition comprises:

a. from about 0.1% to about 12% of a polymeric acid selected from the group consisting of straight poly (acrylic) acid and its copolymers, cross-linked poly (acrylic) acids having a molecular weight of less than 250,000, poly (α-hydroxy) acids, polysulfonic acid and copolymers thereof, and naturally occurring polymeric acids;

b. from about 0.5% to about 80% of a surfactant; and c. from about 3% to about 98.899% of water;

wherein the composition is adjusted to a pH of from about 3.0 to about 6.0.

2. A wipe composition according to claim 1 wherein the polymeric acid is selected from the group consisting of straight-chain poly(acryclic) acids and copolymers thereof, cross-linked poly (acrylic) acids having a molecular weight of less than about 250,000, poly (α-hydroxy) acids and copolymers thereof, polysulfonic acid and copolymers thereof, carageenic acid, carboxy methyl cellulose, and alginic acid.

3. A wipe composition according to claim 2 wherein the surfactant comprises an anionic surfactant.

4. A wipe composition according to claim 3 which comprises from about 5% to about 12% of the polymeric acid.

5. A wipe composition according to claim 4 wherein the pH ranges from about 3.0 to about 5.0.

6. A wipe composition according to claim 5 which additionally comprises from about 0.001% to about 5% of an antimicrobial agent.

7. A wipe composition according to claim 5 which additionally comprises from about 1% to about 30% of a lipophilic skin moisturizing agent.

8. A wipe composition according to claim 6 wherein the antimicrobial agent is selected from the group consisting of 2,4,4'-trichloro-2'-hydroxy-diphenyl ether, 3,4,4'-trichlorocarbanilides, piroctone olamine, PCMX, ZPT, natural essential oils and their key ingredients, and mixtures thereof.

9. A wipe composition according to claim 8 wherein the polymeric acid is selected from the group consisting of poly(acrylic) acid, copolymers thereof and mixtures thereof.

10. A wipe composition according to claim 7 wherein the polymeric acid is selected from the group consisting of poly(acrylic) acid, copolymers thereof and mixtures thereof.

11. A wipe composition according to claim 1 which additionally comprises from about 0.1% to about 10% of a stabilizer.

12. A wipe composition according to claim 1 which additionally comprises from about 0.1% to about 1% of a mildness enhancer.

13. The wipe composition of claim 1, comprising:

a. from about 5% to about 12% of the polymeric acid;

b. from about 5% to about 25% of the surfactant, wherein the surfactant is anionic; and c. from about 65% to about 90% of water;

wherein the composition is adjusted to a pH of from about 3.5 to about 5.0.

14. The wipe composition of claim 1, comprising:

a. from about 5% to about 12% of the polymeric acid;

b. from about 0.1% to about 2% of the surfactant, wherein the surfactant is anionic; and c. from about 38% to about 95% of water;

wherein the composition is adjusted to a pH of from about 3.5 to about 5.0.

* * * * *